(12) United States Patent
Shindo

(10) Patent No.: US 12,102,405 B2
(45) Date of Patent: Oct. 1, 2024

(54) MEDICAL ROBOT, SURGICAL TOOL AND ATTACHMENT PORTION

(71) Applicant: RIVERFIELD INC., Tokyo (JP)

(72) Inventor: Koki Shindo, Tokyo (JP)

(73) Assignee: Riverfield Inc., Tokyo (JP)

( * ) Notice: Subject to any disclaimer, the term of this patent is extended or adjusted under 35 U.S.C. 154(b) by 936 days.

(21) Appl. No.: 17/050,308

(22) PCT Filed: Dec. 20, 2019

(86) PCT No.: PCT/JP2019/050192
§ 371 (c)(1),
(2) Date: Oct. 23, 2020

(87) PCT Pub. No.: WO2021/124572
PCT Pub. Date: Jun. 24, 2021

(65) Prior Publication Data
US 2021/0361370 A1    Nov. 25, 2021

(51) Int. Cl.
*A61B 34/00* (2016.01)
*A61B 34/35* (2016.01)

(52) U.S. Cl.
CPC .............. *A61B 34/71* (2016.02); *A61B 34/35* (2016.02)

(58) Field of Classification Search
CPC .................... A61B 34/71; A61B 34/35; A61B 2017/00477; A61B 34/30
See application file for complete search history.

(56) References Cited

U.S. PATENT DOCUMENTS

2007/0119274 A1    5/2007  Devengenzo et al.
2008/0140088 A1*   6/2008  Orban, III .............. A61B 46/10
                                                606/130

(Continued)

FOREIGN PATENT DOCUMENTS

JP        2009525098 A    7/2009
JP         5283241 B2     9/2013

(Continued)

OTHER PUBLICATIONS

PCT Notification Concerning Documents Transmitted (Form PCT/IB/310) and Translation of Written Opinion (Form PCT/ISA/237) for International Patent Application No. PCT/JP2019/050192, mailed Jan. 15, 2021, 8 pages.

(Continued)

*Primary Examiner* — Richard G Louis
(74) *Attorney, Agent, or Firm* — Withrow + Terranova, PLLC; Vincent K. Gustafson

(57) ABSTRACT

A medical robot of the present disclosure includes: a surgical tool including a treatment portion, and a body including a driven portion configured to transmit a driving force to the treatment portion; and an attachment portion including a transmitting portion configured to transmit the driving force by being engaged with the driven portion, and an attachment surface configured to face the body. The surgical tool includes a surgical-instrument-engagement-part and the attachment portion includes an attachment-portion-engagement-part. The surgical-instrument-engagement-part and the attachment-portion-engagement-part are configured to allow the surgical tool to be attached to the attachment portion by a relative movement of the surgical tool and the attachment portion in a direction along the attachment surface, and also configured to allow the surgical tool to be removed from the attachment portion by a relative movement of the surgical (Continued)

tool and the attachment portion in a direction intersecting with the attachment surface.

6 Claims, 9 Drawing Sheets

(56) References Cited

U.S. PATENT DOCUMENTS

| | | |
|---|---|---|
| 2009/0024142 A1 | 1/2009 | Ruiz Morales |
| 2015/0032151 A1 | 1/2015 | Ishida et al. |
| 2016/0184034 A1 | 6/2016 | Holop et al. |
| 2017/0281161 A1 | 10/2017 | Shelton, IV et al. |
| 2018/0168753 A1 | 6/2018 | Scheib et al. |
| 2019/0000580 A1* | 1/2019 | Scheib .................. A61B 17/00 |
| 2019/0269471 A1 | 9/2019 | Phoolchund et al. |
| 2019/0274766 A1 | 9/2019 | Holop et al. |

FOREIGN PATENT DOCUMENTS

| | | |
|---|---|---|
| JP | 2013215505 A | 10/2013 |
| JP | 2016533910 A | 11/2016 |
| JP | 2019513042 A | 5/2019 |
| JP | 2019529020 A | 10/2019 |
| WO | 2019139841 A1 | 7/2019 |
| WO | 2019195841 A1 | 10/2019 |

OTHER PUBLICATIONS

Extended European Search Report for European Patent Application No. 19925555.5 mailed Oct. 25, 2021, 14 pages.

* cited by examiner

MEDICAL ROBOT, SURGICAL TOOL AND ATTACHMENT PORTION

CROSS-REFERENCE TO RELATED APPLICATION(S)

This application is the U.S. national phase under 35 U.S.C. § 371 of International Application No. PCT/JP2019/050192 filed on Dec. 20, 2019, wherein the entire contents of the foregoing application is hereby incorporated by reference herein.

TECHNICAL FIELD

The present disclosure relates to a medical robot, a surgical tool and an attachment portion.

BACKGROUND ART

Recently, to reduce burden on a practitioner and to save labor in medical facilities, medical treatments using robots have been suggested. In the field of surgery, proposals have been made for medical robots enabling a practitioner to treat a patient by use of a multiple-degree-of-freedom manipulator having a remotely controllable multiple-degree-of-freedom arm (for example, see Patent Document 1).

In the technique described in Patent Document 1, a configuration is disclosed in which a surgical tool for a medical treatment is attachable and removable with respect to a medical robot. Also, a driving force to drive a movable portion of the surgical tool is configured to be transmitted from the medical robot to the surgical tool. The transmission path of this driving force is configured to be engaged and disengaged corresponding to the attachment and the removal of the surgical tool.

As in the case of the medical robot described in Patent Document 1, it is common that a removal path of the surgical tool when the surgical tool is removed from the medical robot is the same as an attaching path when the surgical tool is attached. In other words, by reversely following the attaching path, the surgical tool is removed.

PRIOR ART DOCUMENTS

Patent Documents

Patent Document 1: JP 5283241 B2

SUMMARY OF THE INVENTION

Problems to be Solved by the Invention

However, in some configurations of the medical robots, when a medical robot including a multiple-degree-of-freedom arm takes a specific posture, the attaching/removing path of the surgical tool may be interfered with the medical robot. For example, if the attaching/removing path is interfered with the medical robot that is inoperable, such as in an emergency stop of the medical robot, removing the surgical tool from the medical robot may become impossible or very difficult.

The present disclosure preferably provides a medical robot, a surgical tool and an attachment portion, which realize an easy removal of the surgical tool.

Means for Solving the Problems

A medical robot according to a first mode of the present disclosure includes: a surgical tool including: a treatment portion configured to perform a medical treatment, and a body including at least a driven portion configured to transmit a driving force to the treatment portion; and an attachment portion including at least: a transmitting portion configured to transmit the driving force by being engaged with the driven portion, and an attachment surface from which the transmitting portion is exposed and which is configured to face the body, wherein the surgical tool includes a surgical-instrument-engagement-part, and the attachment portion includes an attachment-portion-engagement-part, wherein the surgical-instrument-engagement-part and the attachment-portion-engagement-part are configured to allow the surgical tool to be attached to the attachment portion by a relative movement of the surgical tool and the attachment portion in a direction along the attachment surface, and also configured to allow the surgical tool to be removed from the attachment portion by a relative movement of the surgical tool and the attachment portion in a direction intersecting with the attachment surface.

A surgical tool according to a second mode of the present disclosure configured to be attached to and removed from an attachment portion, the attachment portion including at least a transmitting portion configured to transmit a driving force by being engaged with a driven portion, and an attachment surface from which the transmitting portion is exposed and which is configured to face the body, the surgical tool comprising: a body including at least: a treatment portion configured to perform a medical treatment, and a driven portion configured to transmit the driving force to the treatment portion; and a surgical-instrument-engagement-part configured to be engaged with and removed from an attachment-portion-engagement-part provided on the attachment portion, wherein the surgical-instrument-engagement-part is configured to allow the surgical tool to be attached to the attachment portion by a relative movement of the surgical tool and the attachment portion in a direction along the attachment surface, and also configured to allow the surgical tool to be removed from the attachment portion by a relative movement of the surgical tool and the attachment portion in a direction intersecting with the attachment surface.

An attachment portion according to a third mode of the present disclosure is configured so that a surgical tool is attached and removed, the surgical tool including a body including at least a treatment portion configured to perform a medical treatment, and a driven portion configured to transmit a driving force to the treatment portion, the attachment portion comprising: a transmitting portion configured to transmit the driving force by being engaged with the driven portion; an attachment surface from which the transmitting portion is exposed and which is configured to face the body; and an attachment-portion-engagement-part configured to be engaged with and removed from a surgical-instrument-engagement-part provided on the surgical tool, wherein the attachment-portion-engagement-part is configured to allow the surgical tool to be attached to the attachment portion by a relative movement of the surgical tool and the attachment portion in a direction along the attachment surface, and also configured to allow the surgical tool to be removed from the attachment portion by a relative movement of the surgical tool and the attachment portion in a direction intersecting with the attachment surface.

With this configuration, the surgical tool includes the surgical-instrument-engagement-part and the attachment portion includes the attachment-portion-engagement-part. Thus, by the relative movement of the surgical tool and the attachment portion in the direction along the attachment surface, the surgical tool is attached to the attachment portion. Also, by the relative movement of the surgical tool and the attachment portion in the direction intersecting with the attachment surface, the surgical tool is removed from the attachment portion.

In the first mode of the above disclosure, it is preferable that the surgical tool includes a surgical-instrument-restrictor, and the attachment portion includes an attachment-portion-restrictor, and the surgical-instrument-restrictor and the attachment-portion-restrictor are configured to restrict a relative position of the surgical tool and the attachment portion in the direction along the attachment surface to the specified position, and configured to allow the relative movement of the surgical tool and the attachment portion in the direction intersecting with the attachment surface.

With this configuration, by providing the surgical-instrument-restrictor and the attachment-portion-restrictor, a position of the attached surgical tool, in the direction along the attachment surface, relative to the attachment portion is restricted to a specified position. In addition, since the relative movement of the surgical tool and the attachment portion in the direction intersecting with the attachment surface is allowed, the surgical-instrument-restrictor and the attachment-portion-restrictor are less likely to be interfered with each other at the time of removing the surgical tool from the attachment portion.

In the first mode of the above disclosure, it is preferable that the attachment surface includes a passage portion configuring a space allowing the surgical-instrument-engagement-part leaving the attachment-portion-engagement-part to move when the surgical tool is removed from the attachment portion.

With this configuration, by providing the passage portion, the surgical-instrument-engagement-part is unlikely to be interfered with the attachment surface at the time of removing the surgical tool from the attachment portion. In addition, it is possible to relatively move the surgical-instrument-engagement-part toward the attachment surface, which facilitates disengagement of the surgical-instrument-engagement-part and the attachment-portion-engagement-part.

Effects of the Invention

According to the medical robot of the first mode, the surgical tool of the second mode, and the attachment portion of the third mode of the present disclosure, the surgical tool includes the surgical-instrument-engagement-part and the attachment portion includes the attachment-portion-engagement-part. Thus, a path to attach the surgical tool to the attachment portion and a path to remove the surgical tool from the attachment portion are different. This exerts an effect of easily removing the surgical tool even when a path at the time of attaching the surgical tool is interfered with an arm of a robot, for example, as in the case of an emergency stop of the medical robot.

EXPLANATION OF REFERENCE NUMERALS

1 . . . medical robot, 20 . . . adapter (attachment portion), 21 . . . attachment surface, 22 . . . transmitting portion, 31 . . . first attachment-portion-engagement-part (attachment-portion-engagement-part), 35 . . . second attachment-portion-engagement-part (attachment-portion-engagement-part), 41 . . . first attachment-portion-restrictor (attachment-portion-restrictor), 46 . . . second attachment-portion-restrictor (attachment-portion-restrictor), 48 . . . pass age portion, 50 . . . surgical tool, 51 . . . body, 53 . . . driven portion, 61 . . . first surgical-instrument-engagement-part (surgical-instrument-engagement-part), 62 . . . second surgical-instrument-engagement-part (surgical-instrument-engagement-part), 67 . . . first surgical-instrument-restrictor (surgical-instrument-restrictor), 68 . . . second surgical-instrument-restrictor (surgical-instrument-restrictor), 75 . . . forceps (treatment portion)

MODE FOR CARRYING OUT THE INVENTION

A medical robot according to one embodiment of the present disclosure will be described with reference to FIG. 1 to FIG. 9. A medical robot 1 of the present embodiment is a multiple-degree-of-freedom manipulator with a remotely controllable multiple-degree-of-freedom arm, and the medical robot 1 can be used by a practitioner to treat a patient, for example, in an endoscopic surgery.

Figure 1:
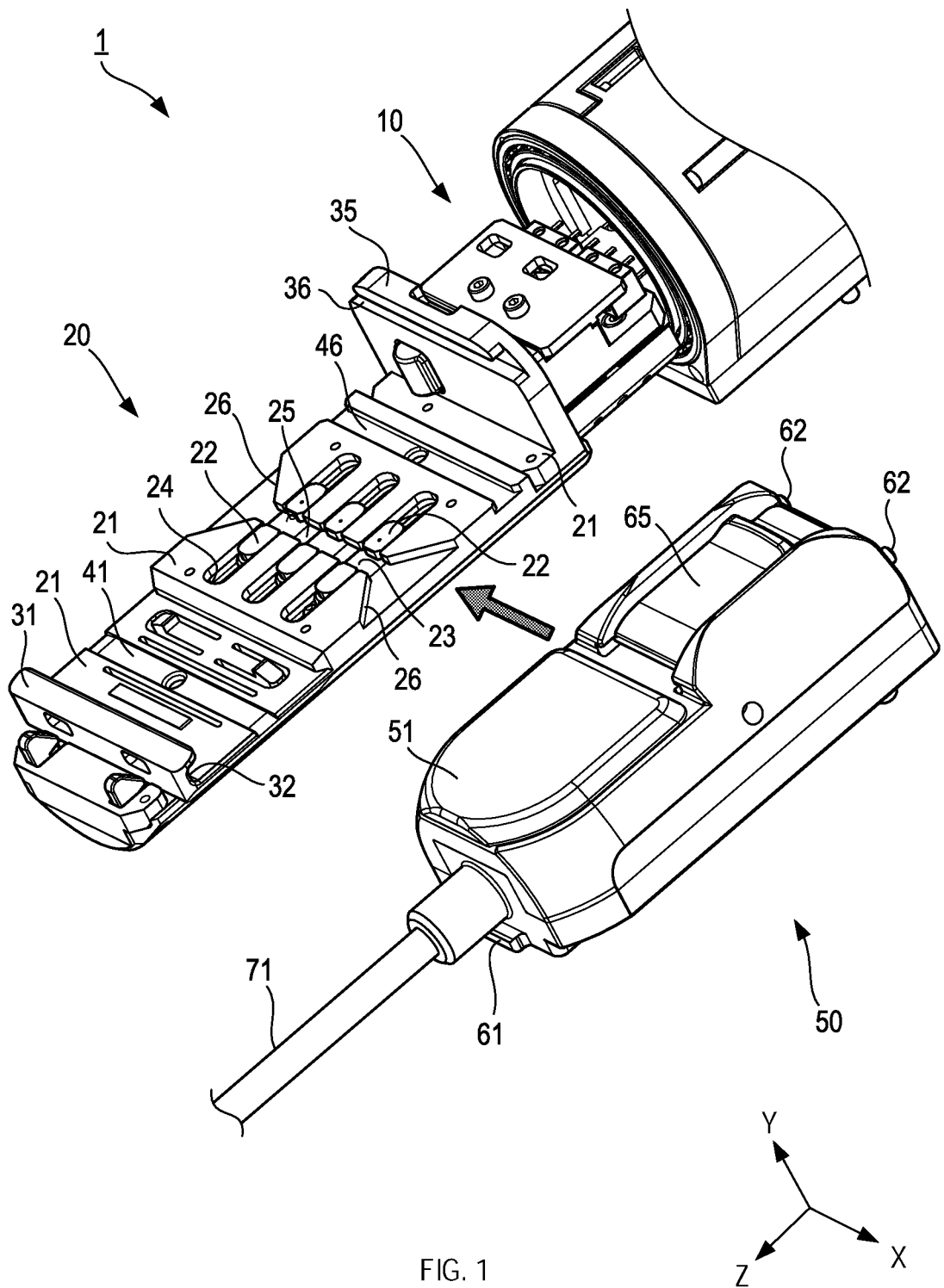
FIG. 1 is a partial perspective view illustrating a configuration of a medical robot according to one embodiment of the present disclosure.

The medical robot 1 includes, as shown in FIG. 1, a driver 10, an adapter 20 (corresponding to an attachment portion), and a surgical tool 50.

In the present embodiment, to simplify the explanation, a direction in which the driver 10 extends is described as a Z-axis and a direction from a rear end portion to the tip of the driver 10 (a direction from the driver 10 to the adapter 20) is described as a positive direction. Also, a direction orthogonal to the Z-axis and along a direction of a relative movement at the time of attaching the surgical tool 50 to the adapter 20 is described as an X-axis. A direction toward left when facing the positive Z-axis direction is described as a positive X-axis direction. Furthermore, a direction orthogonal to the Z-axis and the X-axis is described as Y-axis. A removal direction of the adapter 20 at the time of removing the surgical tool 50 from the adapter 20 is described as a positive Y-axis direction.

The driver 10 supports the adapter 20 and the surgical tool 50, and has a configuration to transmit a driving force to operate the surgical tool 50. In the driver 10, a portion for the adapter 20 to be arranged is configured to be rotatable around an axis extending in a Z-axis direction.

Figure 2:
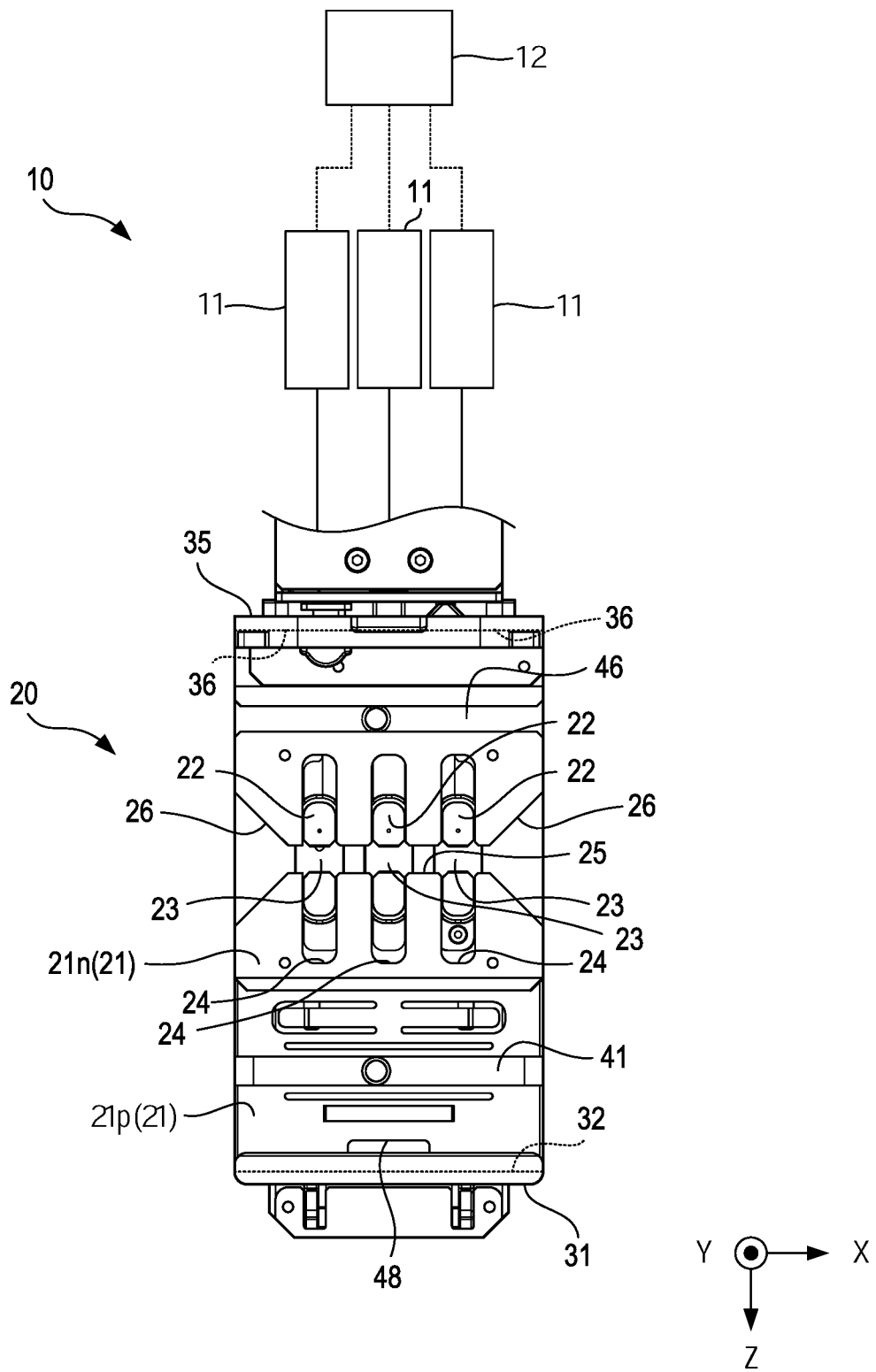
FIG. 2 is a view illustrating a configuration of an arm and an adapter of FIG. 1.

The driver 10 includes, as shown in FIG. 2, multiple (in the present embodiment, three) actuator parts 11(hereinafter, simply referred to as one actuator part 11) and a controller 12. At least either one of the actuator part 11 and the controller 12 may be provided on the driver 10, or may be provided off the driver 10, and the arrangement position thereof may not be limited.

The actuator part 11 has a configuration to generate a driving force to operate the surgical tool 50. The actuator part 11 is connected to one of the below-described multiple (in the present embodiment, three) transmitting portions 22 (hereinafter, simply referred to as one transmitting portion 22) of the adapter 20 so as to be able to transmit the driving force. The actuator 11 has a configuration to move the transmitting portion 22 in the positive Z-axis direction and a negative Z-axis direction.

The actuator part 11 may have a configuration to generate the driving force using gas such as air, or fluid. Alternatively, examples of the actuator part 11 to be used may include an actuator having a configuration using an electric motor. The forms and configurations thereof to generate the force may not be limited.

In addition, examples of the actuator part 11 to be used may include an actuator having a configuration using a piston or a cylinder, and other actuators having a configuration to generate the driving force by fluid, and specific configurations thereof may not be limited.

The controller 12 has a configuration to control the generation of the driving force in the actuator part 11. The controller 12 also has a configuration to control movements of the transmitting portion 22 in the positive and the negative Z-axis direction, and has a configuration to control an arrangement position of the transmitting portion 22. In the present embodiment, the controller 12 controls a supply of gas such as air to the actuator part 11.

The adapter 20 is, as shown in FIG. 1, arranged between the driver 10 and the surgical tool 50. The adapter 20 has a configuration to be attached to and removed from the driver 10, and also attached to and removed from the surgical tool 50.

In addition, the adapter 20 has a configuration to define an unclean area on a driver 10 side and a clean area on a surgical tool 50 side. The adapter 20 includes a drape (not shown) that is a membrane member to define the unclean area and the clean area.

The adapter 20 at lease includes, as shown in FIG. 2, an attachment surface 21, a first attachment-portion-engagement-part 31 (corresponding to an attachment-portion-engagement-part), a second attachment-portion-engagement-part 35 (corresponding to the attachment-portion-engagement-part), a first attachment-portion-restrictor 41 (corresponding to an attachment-portion-restrictor), a second attachment-portion-restrictor 46 (corresponding to an attachment-portion-restrictor), and a passage portion 48.

The attachment surface 21 of the adapter 20 is a surface on which the surgical tool 50 is arranged. The attachment surface 21 is configured to face a surface, on which a driven portion-side hole 52 is provided, of a below-described body 51 of the surgical tool 50. The attachment surface 21 includes the first attachment-portion-engagement-part 31 in the positive Z-axis end portion, and includes the second attachment-portion-engagement-part 35 in the negative Z-axis end portion.

Figure 3:
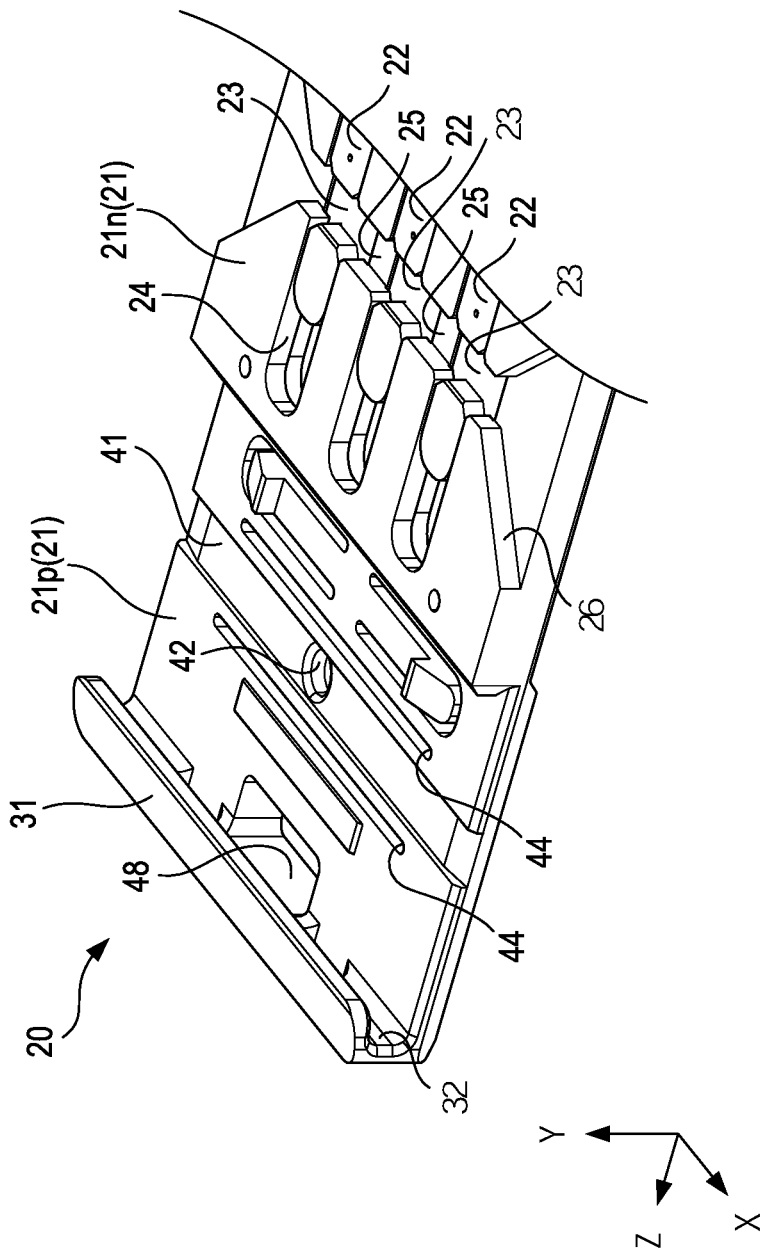
FIG. 3 is a perspective view illustrating a configuration of the adapter of FIG. 1.

As shown in FIG. 2 and FIG. 3, the attachment surface 21 includes a step provided between a region 21$p$ in the positive Z-axis direction and a region 21$n$ in the negative Z-axis direction. In the attachment surface 21, the region 21$n$ in the negative Z-axis direction is more protrude in the positive Y-axis direction than the region 21$p$ in the positive Z-axis direction. In the attachment surface 21, the region 21$p$ in the positive Z-axis direction includes the passage portion 48 and the first attachment-portion-restrictor 41, and the region 21$n$ in the negative Z-axis direction includes the second attachment-portion-restrictor 46.

The adapter 20 further includes at least the transmitting portion 22, multiple (in the present embodiment, three) transmission-side holes 24 (hereinafter, simply referred to as one transmission-side hole 24), a guide groove 25, and two guide portions 26 formed thereon.

The transmitting portion 22 has a configuration to transmit the driving force to the surgical tool 50. In the present embodiment, the transmitting portion 22 has a configuration to transmit the driving force by moving in the positive and the negative Z-axis direction in the transmission-side hole 24.

The transmitting portion 22 includes a recessed portion 23 formed thereon configured to be engaged with a below-described convex 54 of the surgical tool 50. The recessed portion 23 is a recess formed on a surface of the transmitting portion 22 so as to face the surgical tool 50, in other words, a recess formed on a surface on a side of the positive Y-axis direction of the transmitting portion 22.

The recessed portion 23 is formed into a groove extending in the positive Y-axis direction and the negative Y-axis direction. In other words, the recessed portion 23 has an opening configured to allow the below-described convex 54 to enter and exit the recessed portion 23 in the positive Y-axis direction and the negative Y-axis direction.

Also, the recessed portion 23 includes a side wall standing on a side of the positive Z-axis direction and a side wall standing on a side of the negative Z-axis direction. These side walls are shaped to come in contact with the below-described convex 54. In other words, each of the side walls has a shape capable of transmitting movements in the positive Z-axis direction and the negative Z-axis direction in the transmitting portion 22 to the convex 54.

The transmission-side hole 24 is a through-hole. In the transmission-side hole 24, the transmitting portion 22 is arranged so as to be movable relatively to the transmission-side hole 24. In the transmission-side hole 24, the transmitting portion 22 can be moved in the direction along the attachment surface 21. The transmission-side hole 24 is configured such that the transmitting portion 22 does not stray from the transmission-side hole 24. The transmission-side hole 24 is formed into an elongated hole extending in a direction along the Z-axis. In the present embodiment, three transmission-side holes 24 are arranged at intervals in an X-axis direction.

In the present embodiment, an example is described in which there are three pairs of the transmitting portion 22 and the transmission-side hole 24. However, the number of the pair of the transmitting portion 22 and the transmission-side hole 24 may be more than three or less than three, and the number may not be limited.

The guide groove 25 is a recess formed on the attachment surface 21 and used to guide the convex 54 of a below-described driven portion 53. The guide groove 25 is a groove extending in a direction where the surgical tool 50 is moved relatively to the attachment surface 21. In the present embodiment, the guide groove 25 extends in a direction intersecting with the transmission-side hole 24, for example, in a direction along the X-axis.

Two guide portions 26 are grooves continuously formed with the guide groove 25, and the guide portion 26 is located at each of a first end portion and a second end portion of the guide groove 25. The guide portion 26 has a shape in which the groove increases its width toward a direction away from the transmission-side hole 24. It is preferable that opening portions of the two guide portions 26, in other words, a width on an end portion in the positive X-axis direction and a width on an end portion in the negative X-axis direction each have an area to include at least a movement range of the convex 54 in the transmitting portion 22. In the present embodiment, the guide groove 25 has the guide portion 26 at each end portion thereof. However, the guide groove 25 may have the guide portion 26 only on the first end portion or on the second end portion.

The first attachment-portion-engagement-part 31 is formed so as to protrude in the positive Y-axis direction from a positive Z-axis end portion of the attachment surface 21 of the adapter 20. The first attachment-portion-engagement-part 31 is configured to come in contact with the surgical tool 50 arranged on the attachment surface 21 to restrict a movement of the surgical tool 50 in the positive Z-axis direction.

In the first attachment-portion-engagement-part 31, a surface configured to face the surgical tool 50 includes a first engagement groove 32 formed thereon. The first engagement groove 32 is a groove that opens in the negative Z-axis direction and extends along the X-axis. The first engagement groove 32 is configured to be engaged with a below-described first surgical-instrument-engagement-part 61 of the surgical tool 50 to restrict a movement of the surgical tool 50 along a Y-axis direction.

The second attachment-portion-engagement-part 35 is formed so as to protrude in the positive Y-axis direction from a negative Z-axis end portion of the attachment surface 21 of the adapter 20. The second attachment-portion-engagement-part 35 is configured to come in contact with the surgical tool 50 arranged on the attachment surface 21 to restrict a movement of the surgical tool 50 in the negative Z-axis direction.

In the second attachment-portion-engagement-part 35, a surface configured to face the surgical tool 50 includes a second engagement groove 36 formed thereon. The second engagement groove 36 is a groove that opens in the positive Z-axis direction and extends in along the X-axis direction. The second engagement groove 36 is configured to be engaged with a below-described second surgical-instrument-engagement-part 62 of the surgical tool 50 to restrict the movement of the surgical tool 50 along the Y-axis direction.

The first attachment-portion-restrictor 41 has a configuration to restrict, together with a below-described first surgical-instrument-restrictor 67, a relative position of the surgical tool 50 and the adapter 20 in the direction along the attachment surface 21, in other words, in a direction along a Z-X plane to a specified position. The first attachment-portion-restrictor 41 also has a configuration to allow a relative movement in a direction intersecting with the attachment surface 21, in other words, in a Y-axis direction.

The first attachment-portion-restrictor 41 is a groove formed in the region 21p in the positive Z-axis direction of the attachment surface 21 and formed so as to extend in the X-axis direction. The positive X-axis end portion and the negative X-axis end portion of the first attachment-portion-restrictor 41 each have a shape in which the groove increases its depth in the Y-axis direction toward the outer side.

In the center of the X-axis direction of the first attachment-portion-restrictor 41, an engagement recess 42 engaged by the below-described first surgical-instrument-restrictor 67 is formed. The engagement recess 42 is a recess that opens toward the positive Y-axis direction. The engagement recess 42 may have any shape if the engagement recess 42 can be engaged with and disengaged from the first surgical-instrument-restrictor 67. The engagement recess 42 may be a through-hole.

Figure 4:
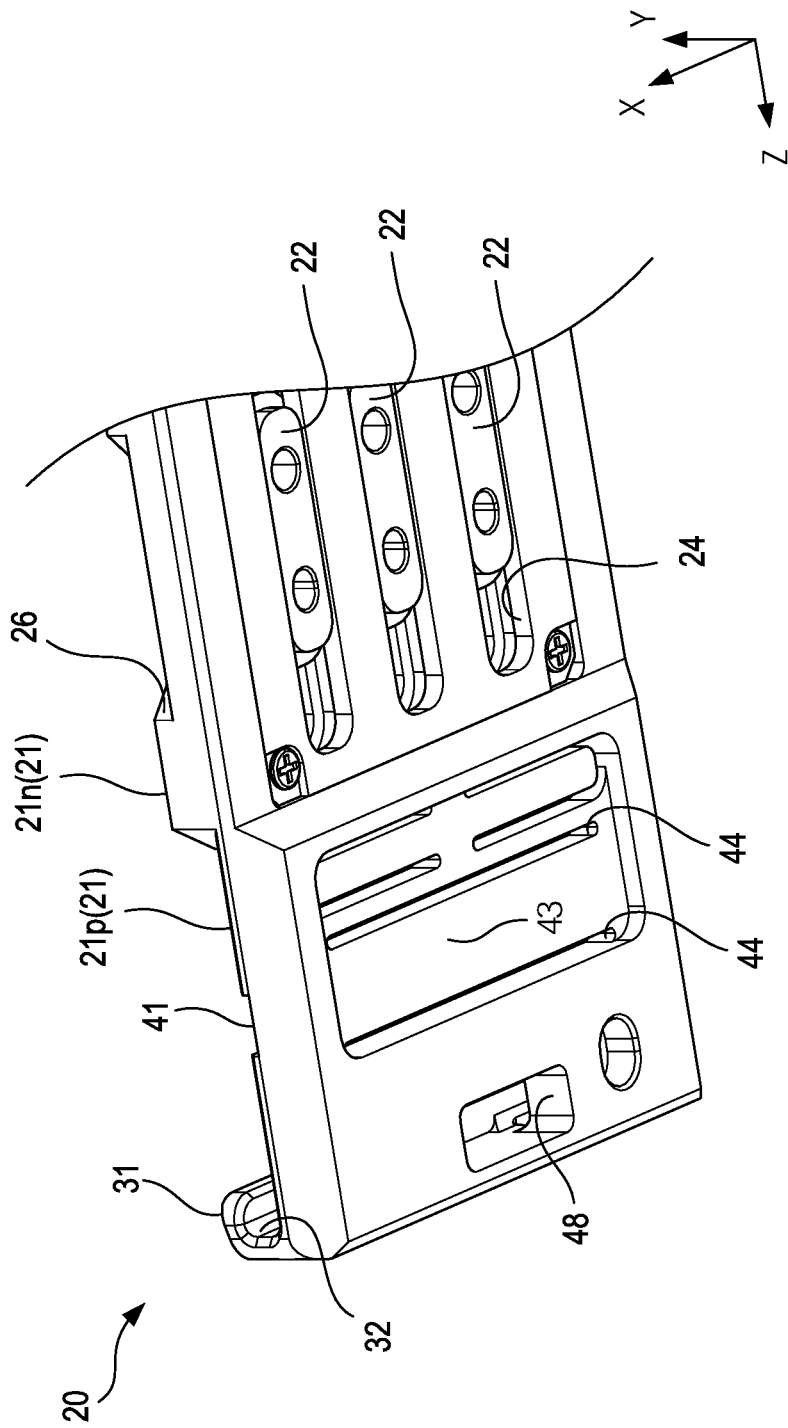
FIG. 4 is another perspective view illustrating a configuration of the adapter of FIG. 1.

On a back surface of the attachment surface 21 of the adapter 20, as shown in FIG. 4, a thickness-reducing portion 43 is formed which is configured to allow a bending deformation of the first attachment-portion-restrictor 41. The thickness-reducing portion 43 is a recessed portion formed in a region corresponding to the first attachment-portion-restrictor 41 on the back surface of the attachment surface 21. A thickness of the first attachment-portion-restrictor 41, in other words, a dimension of the first attachment-portion-restrictor 41 in the Y-axis direction is thinner than that of other portions in the region 21p.

In a position adjacent to the first attachment-portion-restrictor 41 of the region 21p, as shown in FIG. 3 and FIG. 4, two slits 44 are formed so as to extend along the first attachment-portion-restrictor 41. The two slits 44 are through-holes opening to the thickness-reducing portion 43.

The second attachment-portion-restrictor 46 has a configuration to restrict, together with a second surgical-instrument-restrictor 68, a relative position of the surgical tool 50 and the adapter 20 in the direction along the attachment surface 21, in other words, in the direction along the Z-X plane to a specified position. The second attachment-portion-restrictor 46 also has a configuration to allow a relative movement in the direction intersecting with the attachment surface 21, in other words, in the Y-axis direction.

The second attachment-portion-restrictor 46 is a groove formed in the region 21n in the negative Z-axis direction of the attachment surface 21 and formed so as to extend in the X-axis direction. The positive X-axis end portion and the negative X-axis end portion of the second attachment-portion-restrictor 46 each have a shape in which the groove increases its width in the Z-axis direction toward the outer side.

The passage portion 48 forms, at the time of removing the surgical tool 50 from the adapter 20, a space where the below-described first surgical-instrument-engagement-part 61 leaving the first attachment-portion-engagement-part 31 passes. The passage portion 48 is a through-hole formed in the region 21p in the positive Z-axis direction of the attachment surface 21 and formed so as to extend in the Y-axis direction. The passage portion 48 is a through-hole with a rectangular opening when seen from the Y-axis direction. The rectangular opening has an area larger than that of the first surgical-instrument-engagement-part 61 that is a rectangular protrusion.

In the present embodiment, the passage portion 48 is a through-hole; however, the passage portion 48 may be a recessed portion opening in the positive Y-axis direction if configuring a space to allow the first surgical-instrument-engagement-part 61 to move.

Figure 5:
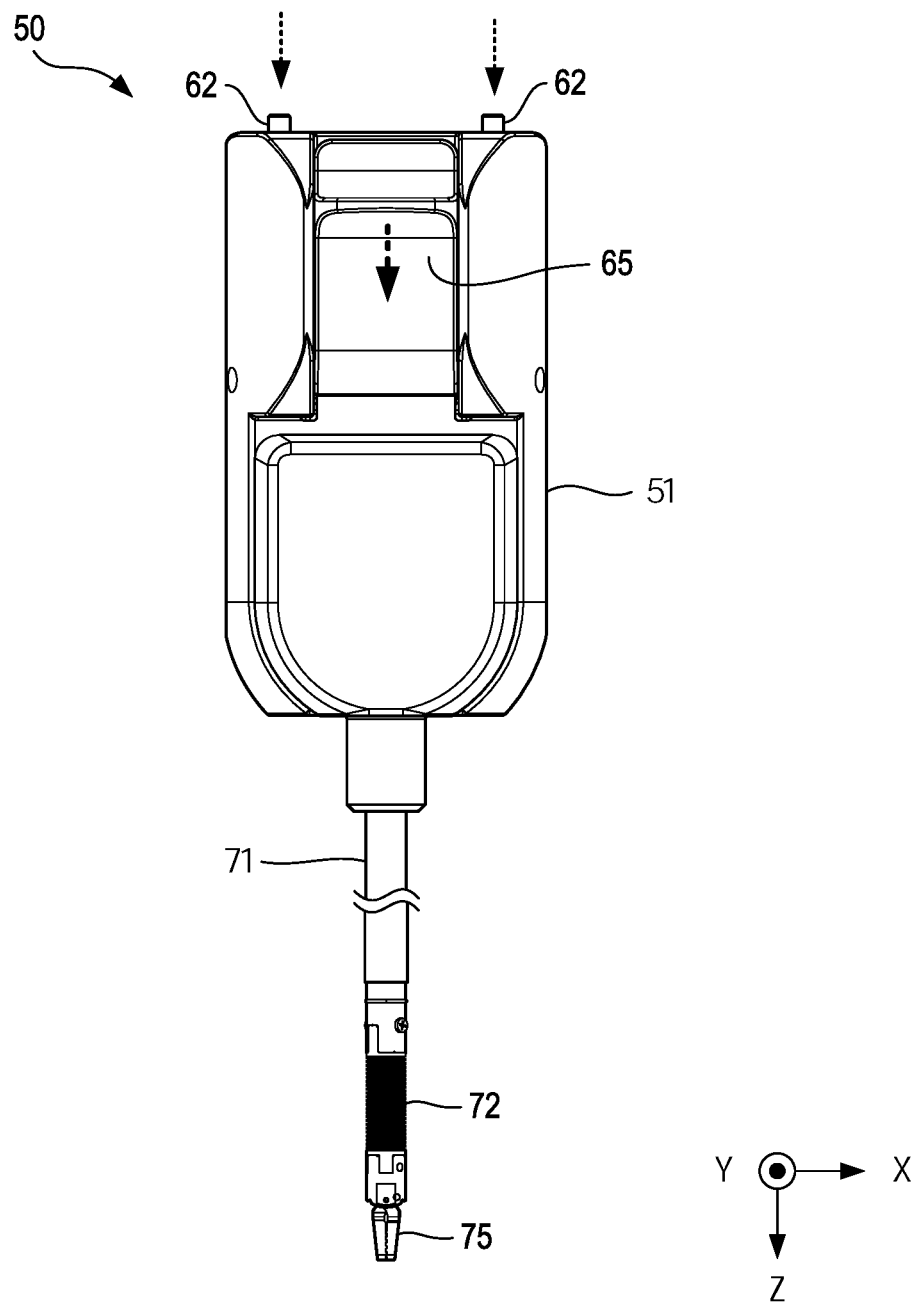
FIG. 5 is a view illustrating a configuration of a surgical tool of FIG. 1.
Figure 6:
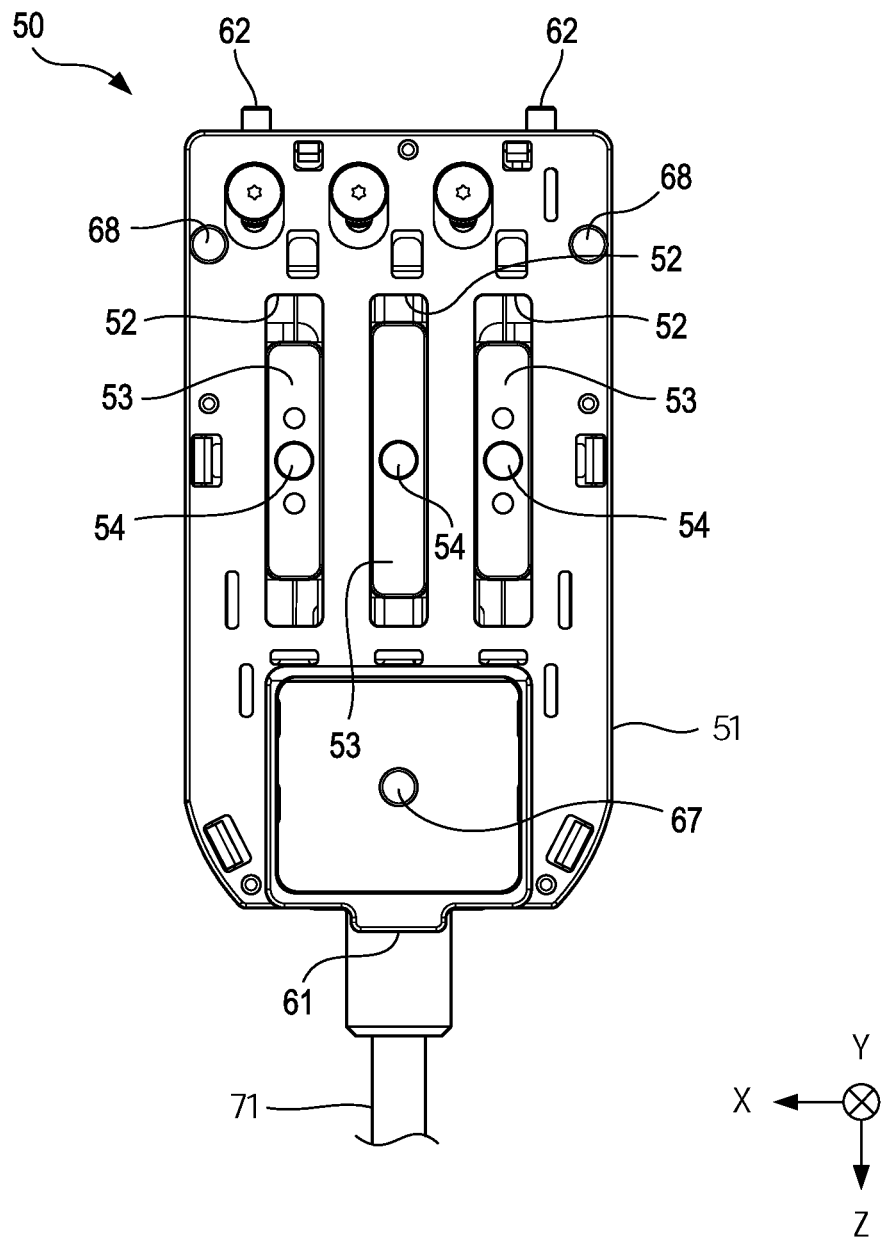
FIG. 6 is another view illustrating a configuration of the surgical tool of FIG. 1.

The surgical tool 50 has a configuration to be used when a practitioner provides a medical treatment to a patient using the medical robot 1. The surgical tool 50 includes, as shown in FIG. 5 and FIG. 6, the body 51, a shaft 71 extending from the body 51, and a forceps 75 (corresponding to a treatment portion) arranged at the end portion of the shaft 71 opposite to the body 51.

The body 51 is configured to be attached to and removed from the adapter 20, and configured to support the shaft 71. The body 51 includes multiple (in the present embodiment, three) driven portion-side holes 52 (hereinafter, simply referred to as one driven portion-side hole 52), multiple (in the present embodiment, three) driven portions 53 (hereinafter, simply referred to as one driven portion 53), the first surgical-instrument-engagement-part 61 (corresponding to a surgical-instrument-engagement-parts 62 (corresponding to the surgical-instrument-engagement-part) (hereinafter, simply referred to as one second surgical-instrument-engagement-part 62), an operation portion 65, the first surgical-instrument-restrictor 67 (corresponding to a surgical-instrument-restrictor), two second surgical-instrument-restrictors 68 (corresponding to the surgical-instrument-restrictor) (hereinafter, simply referred to as one second surgical-instrument-restrictor 68).

The driven portion-side hole 52 is an elongated hole formed on a surface of the body 51 configured to face the attachment surface 21 and formed so as to extend in the Z-axis direction. The driven portion-side hole 52 is formed at a position configured to face the transmission-side hole 24. In the driven portion-side hole 52, the below-described driven portion 53 is arranged so as to be movable relatively to the body 51 linearly in the Z-axis direction. In the present embodiment, an example is described in which three driven portion-side holes 52 are arranged at intervals in the X-axis direction.

The driven portion 53 has a configuration in which the driving force to drive the forceps 75 and the like is transmitted from the driver 10. The driven portion 53 is arranged so as to be movable linearly in the Z-axis direction within the driven portion-side hole 52 by the driving force transmitted from a surgical robot.

The driven portion 53 includes the convex 54 formed thereon. The convex 54 is a pillar-shaped portion protruding in the negative Y-axis direction from the driven portion 53. When the driven portion 53 is arranged in the driven portion-side hole 52, the convex 54 protrudes in the negative Y-axis direction more than the body 51. The convex 54 has a configuration to be engaged with the recessed portion 23 provided in the transmitting portion 22 of the adapter 20 to transmit the driving force for the linear movement in the Z-axis direction.

The first surgical-instrument-engagement-part 61 is, as shown in FIG. 6, a rectangular protrusion provided on the positive Z-axis end portion of the body 51. The first surgical-instrument-engagement-part 61 is configured to be engaged with the first engagement groove 32 of the first attachment-portion-engagement-part 31 to restrict the movement of the surgical tool 50 along the Y-axis direction.

The second surgical-instrument-engagement-part 62 is, as shown in FIG. 5 and FIG. 6, a protrusion provided on the negative Z-axis end portion of the body 51. The second surgical-instrument-engagement-part 62 is configured to be engaged with the second engagement groove 36 of the second attachment-portion-engagement-part 35 to restrict the movement of the surgical tool 50 along the Y-axis direction.

The operation portion 65 is, as shown in FIG. 5, a portion to be used when the second surgical-instrument-engagement-part 62 is housed in and projected out from the body 51. The operation portion 65 is provided on a positive Y-axis side surface of the body 51 and located in a negative Z-axis side region of the body 51.

The operation portion 65 is arranged so as to be movable relatively to the body 51 along the Z-axis direction. For example, when the operation portion 65 is moved in the positive Z-axis direction with respect to the body 51, the second surgical-instrument-engagement-part 62 is housed in the body 51. Conversely, when the operation portion 65 is moved in the negative Z-axis direction with respect to the body 51, the second surgical-instrument-engagement-part 62 is protruded from the body 51.

The first surgical-instrument-restrictor 67 is, in the body 51, formed on a surface configured to face the attachment surface 21 at a position corresponding to the first attachment-portion-restrictor 41 and the engagement recess 42 (see FIG. 3 and FIG. 6). The first surgical-instrument-restrictor 67 protrudes in the negative Y-axis direction and has a shape engaged with and disengaged from the first attachment-portion-restrictor 41 and the engagement recess 42. In the present embodiment, an example is described in which the first surgical-instrument-restrictor 67 has a cylindrical shape and protrudes.

The second surgical-instrument-restrictor 68 is, in the body 51, formed on a surface configured to face the attachment surface 21 at a position corresponding to the second attachment-portion-restrictor 46. In the present embodiment, the second surgical-instrument-restrictor 68 is provided on each X-axis end portion of the body 51. The second surgical-instrument-restrictor 68 protrudes in the negative Y-axis direction, and has a shape capable of being engaged with and disengaged from the second attachment-portion-restrictor 46. In the present embodiment, an example is described in which the second surgical-instrument-restrictor 68 has the cylindrical shape and protrudes.

The shaft 71 is, as shown in FIG. 5 and FIG. 6, a tubular member arranged so as to extend in the Z-axis direction from the body 51. On the positive Z-axis end portion of the shaft 71, the forceps 75 is provided. In the vicinity of the forceps 75 of the shaft 71, a joint portion 72 is provided.

The joint portion 72 has a configuration capable of changing an orientation of the forceps 75, and has a configuration capable of rotating about each of the X-axis and the Y-axis as rotating axes. The joint portion 72 has, for example, a configuration to be rotated by the driving force transmitted by the transmitting portion 22. The configuration of the joint portion 72 may include a known configuration and may not be especially limited.

The forceps 75 is arranged on the positive Z-axis end portion of the shaft 71. The forceps 75 has a configuration to be opened and closed by the driving force transmitted from the driven portion 53 via a wire or the like. The configuration to open and close the forceps 75 may include a known configuration, and may not be especially limited.

Next, a description is made in which the surgical tool 50 is attached to and removed from the medical robot 1 having the above configurations. First, attaching the surgical tool 50 to the adapter 20 is described, and then removing the surgical tool 50 from the adapter 20 is described.

When the surgical tool 50 is attached to the adapter 20, as shown in FIG. 2, the controller 12 controls and drives the actuator part 11 so that the transmitting portion 22 is arranged at a predetermined position. When the transmitting portion 22 is arranged at the predetermined position, the recessed portion 23 and the guide groove 25 of the transmitting portion 22 form one groove extending along the X-axis direction.

Here, the predetermined position is a position where the recessed portion 23 of the transmitting portion 22 is arranged at an intersecting position of the guide groove 25 and the transmission-side hole 24. In other words, the predetermined position is a position where the driven portion 53 and the transmitting portion 22 are engaged when the surgical tool 50 is attached to the adapter 20. Specifically, an arrangement position of the transmitting portion 22 shown in FIG. 2 is the predetermined position.

Then, as shown in FIG. 1, the surgical tool 50 is moved along the X-axis direction so as to be brought closer to the adapter 20, whereby the surgical tool 50 is attached. FIG. 1 illustrates an example in which the surgical tool 50 is moved and attached from a positive side to a negative side of the X-axis. It should be noted that the surgical tool 50 may be moved and attached to the adapter 20 from the negative side to the positive side of the X-axis.

At the time of attaching the surgical tool 50, the first surgical-instrument-engagement-part 61 of the surgical tool 50 is engaged with the first engagement groove 32 of the adapter 20 while being moved along the X-axis direction. Also, the second surgical-instrument-engagement-part 62 is engaged with the second engagement groove 36 of the adapter 20 while being moved along the X-axis direction.

Figure 7:
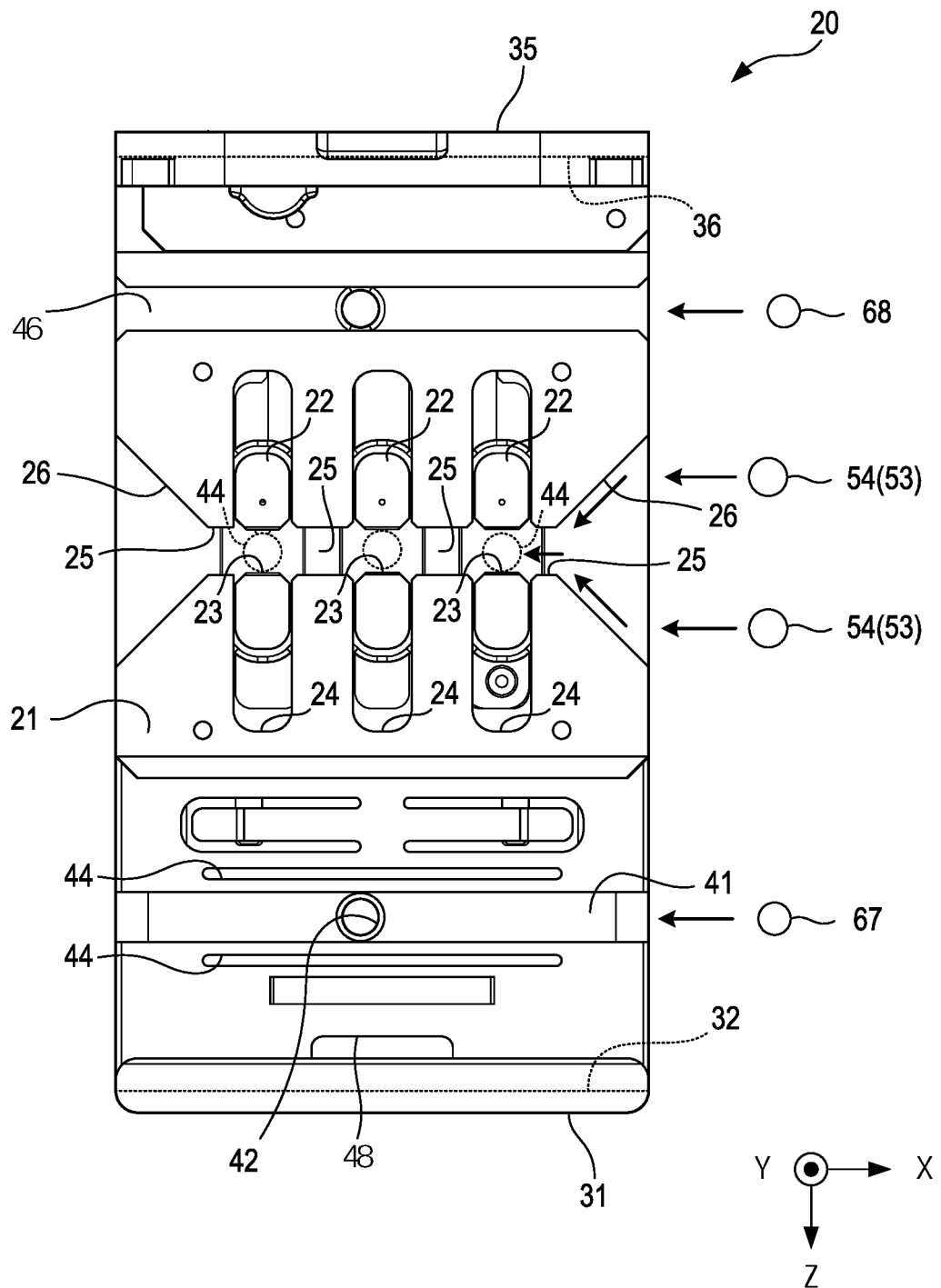
FIG. 7 is a view illustrating a movement when the surgical tool is attached to the adapter.

Furthermore, the driven portion 53 of the surgical tool 50 is, as shown in FIG. 7, guided by the guide groove 25 and the guide portion 26 to a position where the driving force is transmittable between the transmitting portions 22. For example, a description is made of a case where the driven portion 53 is arranged on a positive Z-axis side or a negative Z-axis side and spaced apart from the guide groove 25.

When the surgical tool 50 approaches the adapter 20 along the X-axis, the convex 54 of the driven portion 53 comes in contact with a slope surface of the guide portion 26. When the surgical tool 50 is further moved, the convex 54 of the driven portion 53 is moved toward the guide groove 25 along the slope surface of the guide portion 26 to enter the groove formed by the guide groove 25 and the recessed portion 23.

Also, when the surgical tool 50 approaches the adapter 20 along the X-axis, the second surgical-instrument-restrictor 68 enters the groove of the second attachment-portion-restrictor 46. When the surgical tool 50 is further moved, the first surgical-instrument-restrictor 67 enters the groove of the first attachment-portion-restrictor 41.

The first surgical-instrument-restrictor 67 is moved within the first attachment-portion-restrictor 41 while pressing down the bottom surface of the first attachment-portion-restrictor 41 in the negative Y-axis direction. Specifically, since the first attachment-portion-restrictor 41 is thinner than other regions and includes the two slits 44 adjacent to the first attachment-portion-restrictor 41, the first attachment-portion-restrictor 41 is easily deformed in the Y-axis direction. In other words, the first attachment-portion-restrictor 41 can be deformed in the negative Y-axis direction by the pressing force of the first surgical-instrument-restrictor 67. Thus, the first surgical-instrument-restrictor 67 can be moved within the first attachment-portion-restrictor 41 while pressing down the bottom surface of the first attachment-portion-restrictor 41 in the negative Y-axis direction.

When the first surgical-instrument-restrictor 67 is moved to a position facing the engagement recess 42, the first surgical-instrument-restrictor 67 enters the engagement recess 42 (in other words, the first surgical-instrument-restrictor 67 is engaged with the engagement recess 42 of the first attachment-portion-restrictor 41), and the pressing force against the first attachment-portion-restrictor 41 disappears and the bottom surface of the first attachment-portion-restrictor 41, which is pressed down, returns to the positive Y-axis direction. The first surgical-instrument-restrictor 67 and the engagement recess 42, which are engaged with each other, restrict a relative movement of the adapter 20 and the surgical tool 50 in the X-axis direction.

When the surgical tool 50 is moved to a predetermined position of the adapter 20, the convex 54 is arranged in the recessed portion 23. In other words, the convex 54 is arranged at a position shown by a dotted line in FIG. 7. In the present embodiment, a description is made of an example in which a position where the first surgical-instrument-restrictor 67 and the engagement recess 42 are engaged is the predetermined position. Accordingly, the transmitting portion 22 and the driven portion 53 are engaged with each other so as to transmit the driving force, and the operation to attach the surgical tool 50 and the adapter 20 to each other is completed.

To remove the surgical tool 50 from the adapter 20, first, as shown in FIG. 5, an operation is performed to slide the operation portion 65 of the surgical tool 50 in the positive Z-axis direction. With this operation, the second surgical-instrument-engagement-part 62 is housed in the body 51. The housed second surgical-instrument-engagement-part 62 is disengaged from the second engagement groove 36 (see FIG. 8).

Figure 8:
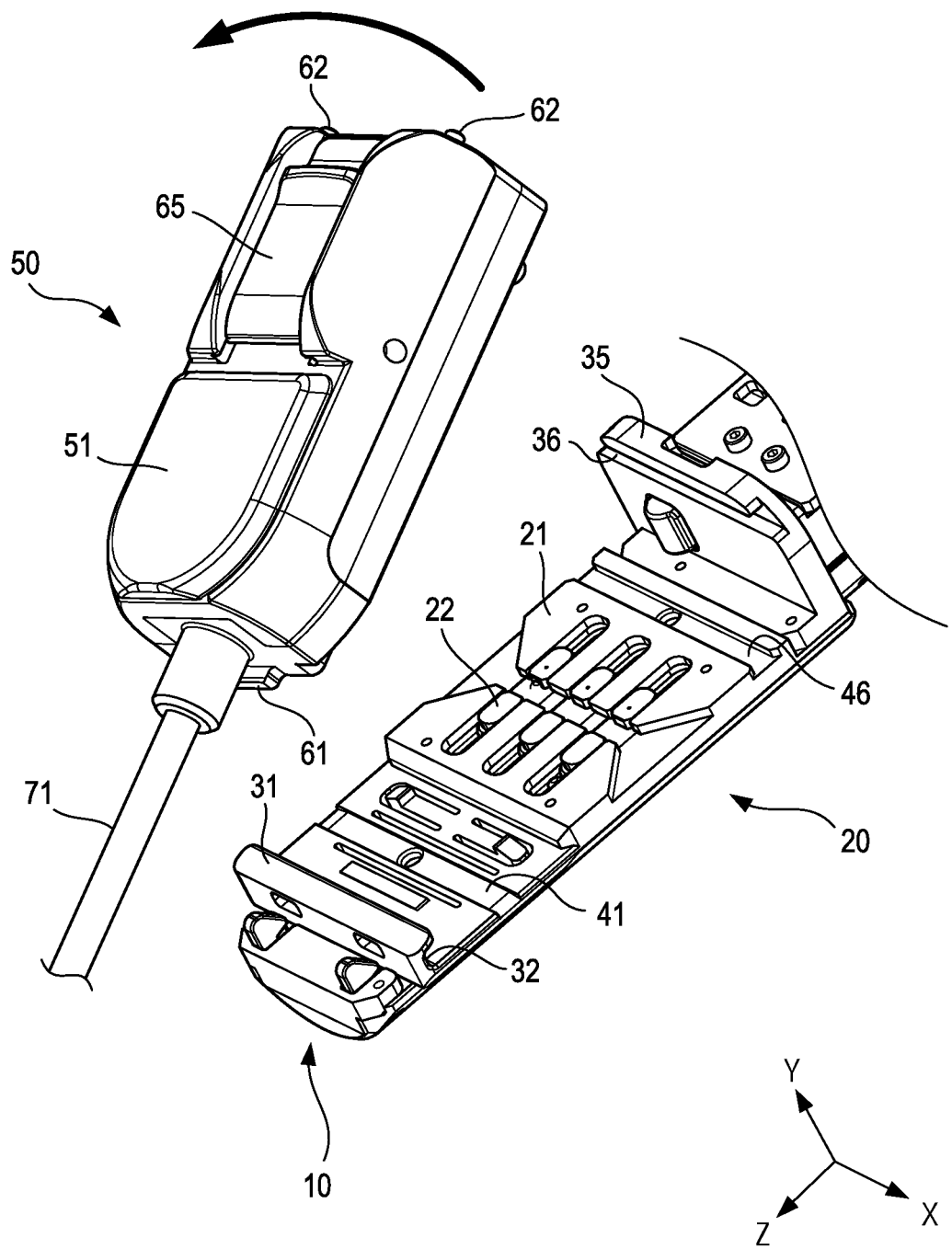
FIG. 8 is a view illustrating a removal of the surgical tool.
Figure 9:
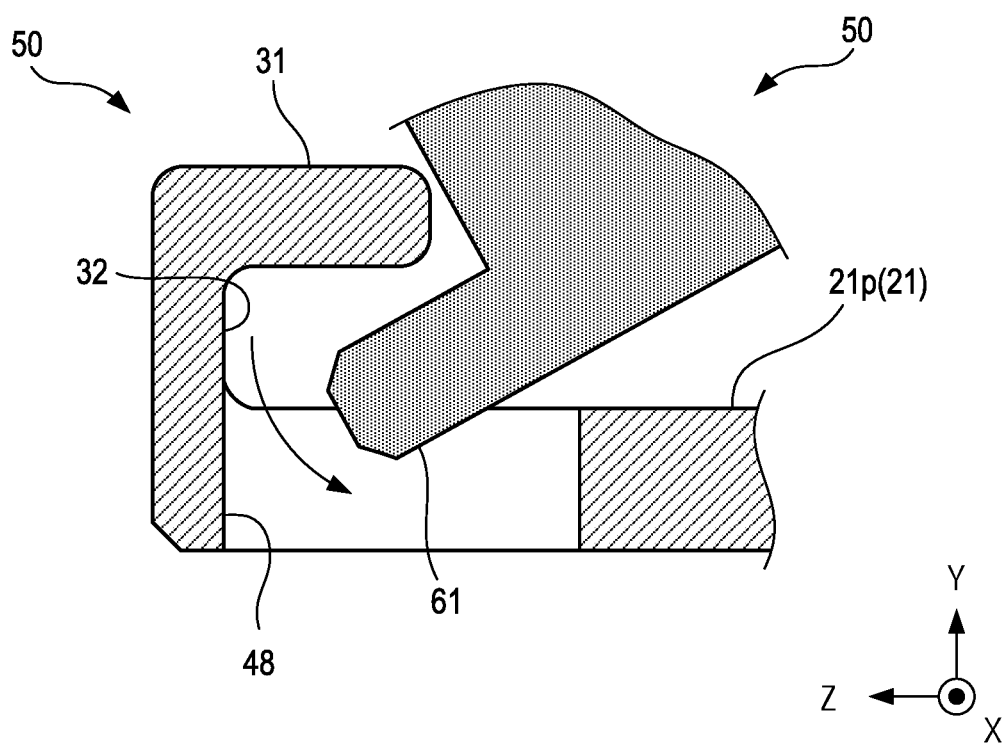
FIG. 9 is a view illustrating a movement of a first surgical-instrument-engagement-part when the surgical tool is removed.

Then, as shown in FIG. 8, an end portion of the surgical tool 50 on a negative Z-axis side is lifted in a direction away from the adapter 20, in other words, in the substantially positive Y-axis direction. At this time, the end portion of the first surgical-instrument-engagement-part 61 rotates, as shown in FIG. 9, in the substantially negative Y-axis direction. In other words, the end portion of the first surgical-instrument-engagement-part 61 enters the passage portion 48.

The first surgical-instrument-restrictor 67 rotates, as shown in FIG. 7 and FIG. 8, in the substantially positive Y-axis direction and disengaged from the first attachment-portion-restrictor 41 and the engagement recess 42 with which the first surgical-instrument-restrictor 67 is engaged. The second surgical-instrument-restrictor 68 rotates in the substantially positive Y-axis direction and disengaged from the second attachment-portion-restrictor 46 with which the second surgical-instrument-restrictor 68 is engaged.

Then, as shown in FIG. 8, a whole body of the surgical tool 50 is lifted in the substantially positive Y-axis direction. At this time, the first surgical-instrument-engagement-part 61 is pulled up and separated from the first engagement groove 32 and the passage portion 48. Accordingly, the operation to remove the surgical tool 50 from the adapter 20 is completed.

According to the medical robot 1 with the above configuration, the surgical tool 50 includes the first surgical-instrument-engagement-part 61 and the second surgical-instrument-engagement-part 62, and the adapter 20 includes the first attachment-portion-engagement-part 31 and the second attachment-portion-engagement-part 35. By the relative movement of the surgical tool 50 and the adapter 20 in the direction along the attachment surface 21, the surgical tool 50 is attached to the adapter 20. Also, by the relative movement of the surgical tool 50 and the adapter 20 in the direction substantially intersecting with the attachment surface 21, the surgical tool 50 is removed from the adapter 20.

By providing the first surgical-instrument-engagement-part 61 and the second surgical-instrument-engagement-part 62, and the first attachment-portion-engagement-part 31 and the second attachment-portion-engagement-part 35, a relative position (a relative position with respect to the adapter 20 in the direction along the attachment surface 21) of the surgical tool 50 attached to the adapter 20 is restricted to the specified position. Since a relative movement (a relative movement of the surgical tool 50 and the adapter 20) in the direction substantially intersecting with the attachment surface 21 is allowed, the first surgical-instrument-engagement-part 61 and the first attachment-portion-engagement-part 31 are less likely to be interfered with each other, and the second surgical-instrument-engagement-part 62 and the second attachment-portion-engagement-part 35 are less likely to be interfered with each other when the surgical tool 50 is removed from the adapter 20.

By providing the passage portion 48, the first surgical-instrument-engagement-part 61 is less likely to be interfered with the attachment surface 21 when the surgical tool 50 is removed from the adapter 20. Also, the first surgical-instrument-engagement-part 61 can be moved relatively to the attachment surface 21, which facilitates disengagement of the first surgical-instrument-engagement-part 61 from the first attachment-portion-engagement-part 31.

It is to be noted that a technical scope of the present disclosure is not limited to the above embodiment, and various modifications may be added without departing from the spirit of the present disclosure. For example, in the above embodiment, a configuration is described in which the surgical tool 50 may be attached from either positive X-axis side or the negative X-axis side. However, the surgical tool 50 may be configured to be attachable only from the positive X-axis side, or may be configured to be attachable only from the negative X-axis side.

Also, in the present embodiment, an explanation has been made in which the driver 10 and the adapter 20 are attachable and removable. However, a component corresponding to the adapter 20 may be united into the driver 10, and the configuration may not be especially limited.

The invention claimed is:

1. A medical robot comprising:
a surgical tool including:
a treatment portion configured to perform a medical treatment, and
a body including at least a driven portion configured to transmit a driving force to the treatment portion; and
an attachment portion including at least:
a transmitting portion configured to transmit the driving force by being engaged with the driven portion, and
an attachment surface from which the transmitting portion is exposed and which is configured to face the body,
wherein the surgical tool includes a surgical-instrument-engagement-part, and the attachment portion includes an attachment-portion-engagement-part,
wherein the surgical-instrument-engagement-part and the attachment-portion-engagement-part are configured to allow the surgical tool to be attached to the attachment portion by a relative movement of the surgical tool and the attachment portion in a direction along the attachment surface, and also configured to allow the surgical tool to be removed from the attachment portion by moving the surgical-instrument-engagement-part engaged with the attachment-portion-engagement-part relative to the body to thereby disengage the surgical-instrument-engagement-part from the attachment-portion-engagement-part, and by a relative movement of the surgical tool and the attachment portion in a direction intersecting with the attachment surface, and
wherein the surgical-instrument-engagement-part is formed as at least one protrusion protruding from an end of the body in a direction along the attachment surface, the at least one protrusion being configured to be engaged with the attachment portion, and the at least one protrusion being configured to be housed in the body.

2. The medical robot according to claim 1,
wherein the surgical tool includes a surgical-instrument-restrictor, and the attachment portion includes an attachment-portion-restrictor,
wherein the surgical-instrument-restrictor and the attachment-portion-restrictor are configured to restrict a relative position of the surgical tool and the attachment portion in the direction along the attachment surface to a specified position, and also configured to allow the relative movement of the surgical tool and the attachment portion in the direction intersecting with the attachment surface.

3. The medical robot according to claim 1,
wherein the attachment surface includes a passage portion configuring a space allowing the surgical-instrument-engagement-part leaving the attachment-portion-engagement-part to move when the surgical tool is removed from the attachment portion.

4. A surgical tool configured to be attached to and removed from an attachment portion, the attachment portion including at least a transmitting portion configured to transmit a driving force by being engaged with a driven portion, and an attachment surface from which the transmitting portion is exposed and which is configured to face a body, the surgical tool comprising:
the body including at least:
a treatment portion configured to perform a medical treatment, and
the driven portion configured to transmit the driving force to the treatment portion; and
a surgical-instrument-engagement-part configured to be engaged with and removed from an attachment-portion-engagement-part provided on the attachment portion,
wherein the surgical-instrument-engagement-part is configured to allow the surgical tool to be attached to the attachment portion by a relative movement of the surgical tool and the attachment portion in a direction along the attachment surface, and also configured to allow the surgical tool to be removed from the attachment portion by moving the surgical-instrument-engagement-part engaged with the attachment-portion-engagement-part relative to the body to thereby disengage the surgical-instrument-engagement-part from the attachment-portion-engagement-part, and by a relative movement of the surgical tool and the attachment portion in a direction intersecting with the attachment surface, and
wherein the surgical-instrument-engagement-part is formed as at least one protrusion protruding from an end of the body in a direction along the attachment surface, the at least one protrusion being configured to be engaged with the attachment portion, and the at least one protrusion being configured to be housed in the body.

5. The medical robot according to claim 1,
wherein the attachment portion includes an engagement recess as the attachment-portion-engagement-part,
wherein the surgical-instrument-engagement-part has a protruding cylindrical shape, and
wherein a movement of the attachment portion and the surgical tool relative to each other is restricted by the surgical-instrument-engagement-part entering the engagement recess.

6. The medical robot according to claim 2,
wherein the medical robot further comprises one or more slits extending along the attachment-portion-restrictor.

* * * * *